United States Patent [19]

Stuhl

[11] 3,986,513

[45] Oct. 19, 1976

[54] APPARATUS FOR IRRADIATING THE SKIN

[76] Inventor: Joseph Lester Stuhl, 101 Serpentine Lane, New York, N.Y. 11507

[22] Filed: Jan. 29, 1976

[21] Appl. No.: 653,593

[52] U.S. Cl. ............................... 128/373; 128/395
[51] Int. Cl.[2] ......................................... A61H 33/06
[58] Field of Search .......... 128/371, 373, 362, 395, 128/396, 24.1, 1 B

[56] References Cited
UNITED STATES PATENTS

| | | | |
|---|---|---|---|
| 558,394 | 4/1896 | Kellogg | 128/373 |
| 664,081 | 12/1900 | Gohlin | 128/373 |
| 1,476,073 | 12/1923 | Guggenbuhl | 128/373 X |
| 2,060,842 | 11/1936 | Yaglou | 128/373 UX |
| 2,184,418 | 12/1939 | Faigle | 128/373 |
| 2,539,900 | 1/1951 | Duffy | 128/1 B |
| 2,960,986 | 11/1960 | Gibbons | 128/373 |
| 3,877,437 | 4/1975 | Maitan et al. | 128/1 B X |

*Primary Examiner*—Lawrence W. Trapp
*Attorney, Agent, or Firm*—Kenyon & Kenyon

[57] ABSTRACT

An apparatus for treating the skin of a patient by irradiating the patient with a light or heat source, particularly in the treatment of psoriasis, comprising:

a. a base;

b. a substantially horizontal support member mounted on said base;

c. a first planar upper radiation unit positioned at one side of said support member in a plane extending upwardly from the upper portion of said support member, said first unit comprising a radiation source and a radiation transmissive material disposed between said radiation source and said support member;

d. an assembly of at least one other upper planar radiation unit comprising a radiation source and a radiation transmissive material; the one other upper radiation unit of the assembly being pivotably mounted with respect to the upper portion of the first radiation unit for movement about a substantially horizontal axis extending adjacent the plane in which the first radiation unit extends; means for selectively retaining the one other upper radiation unit of the assembly in a stored position extending upwardly with respect to the first upper radiation unit and in operating position extending in a facing relationship with the upper surface of the support member, each other upper radiation unit of the assembly being attached to the edge portion of the upper radiation unit adjacent thereto which is nearest the first upper radiation unit.

26 Claims, 7 Drawing Figures

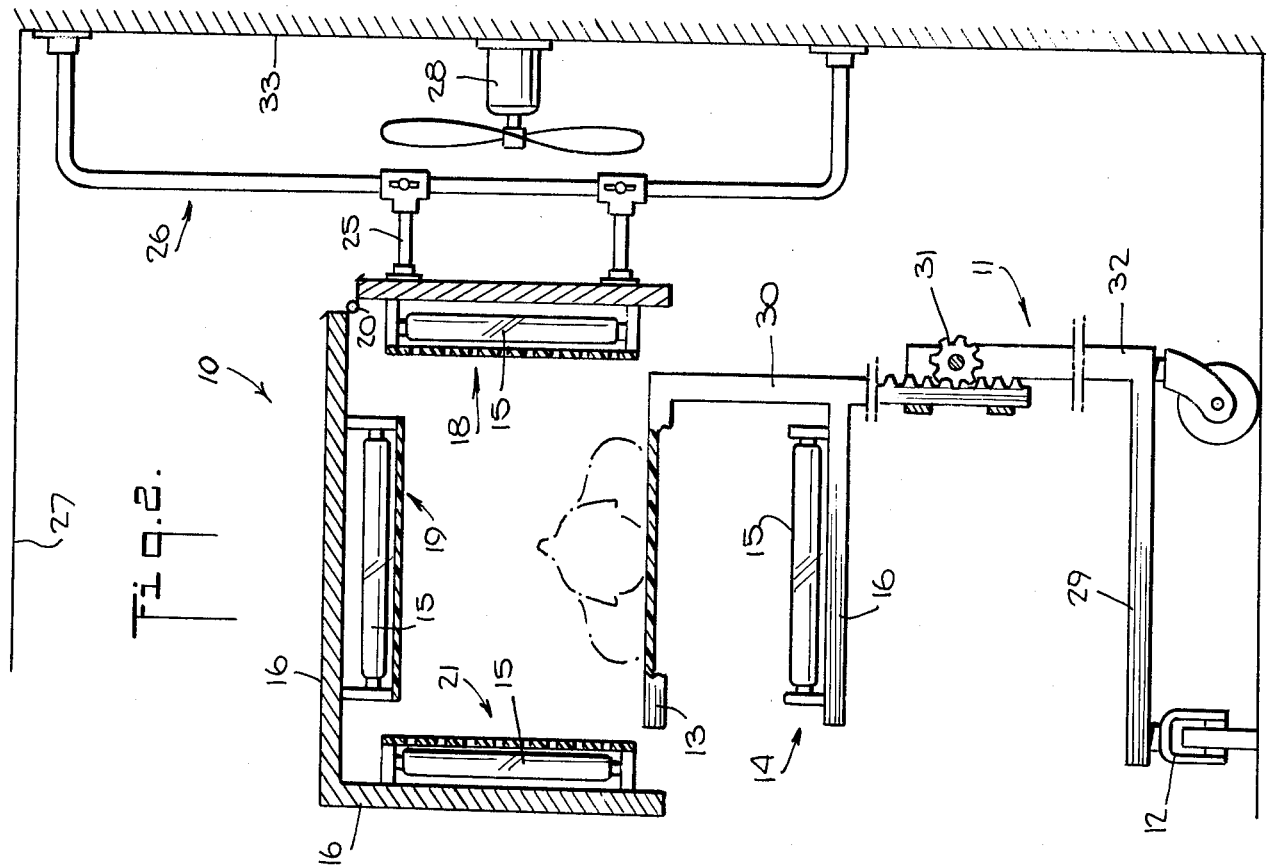
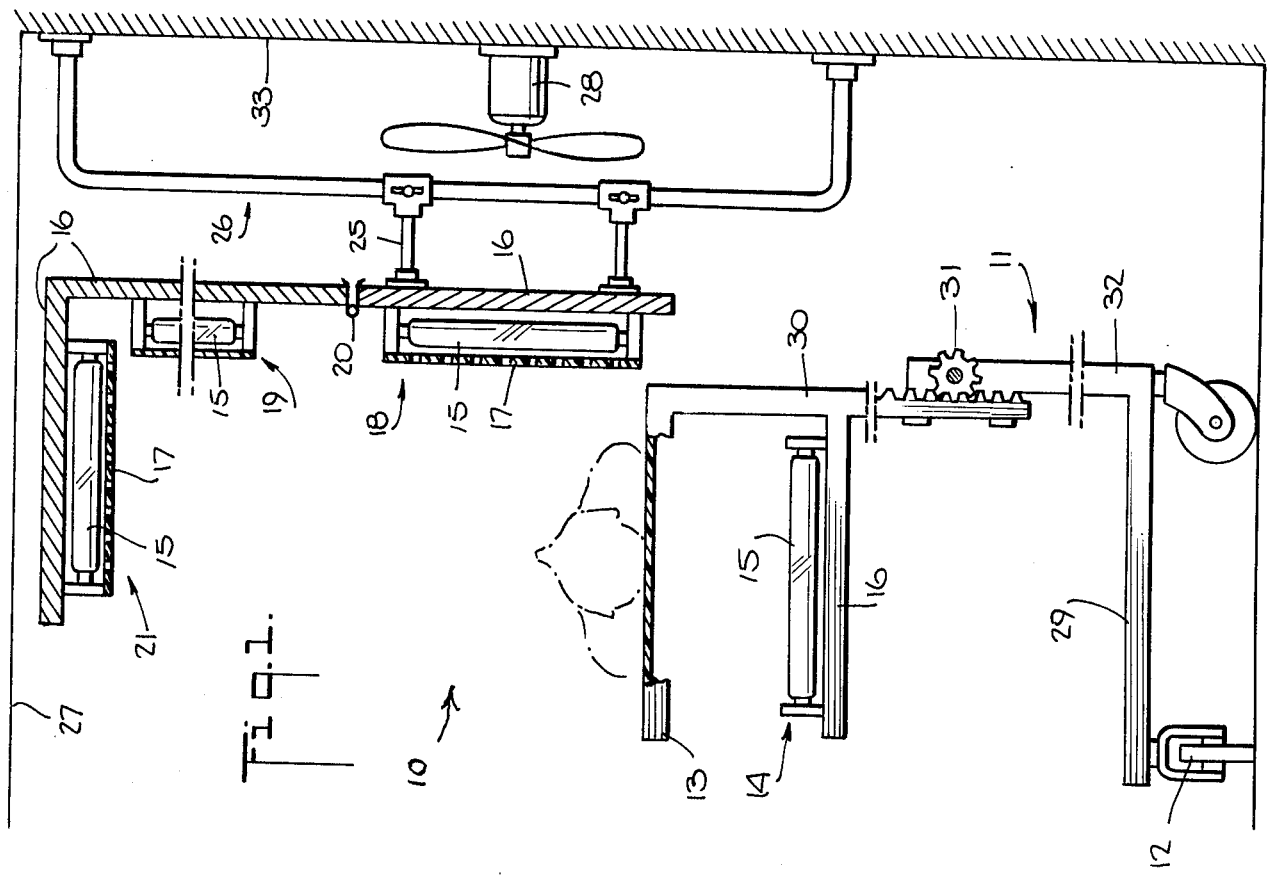

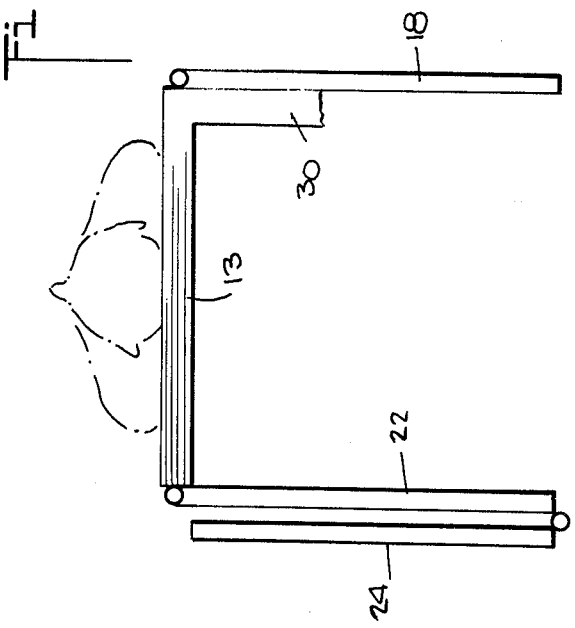
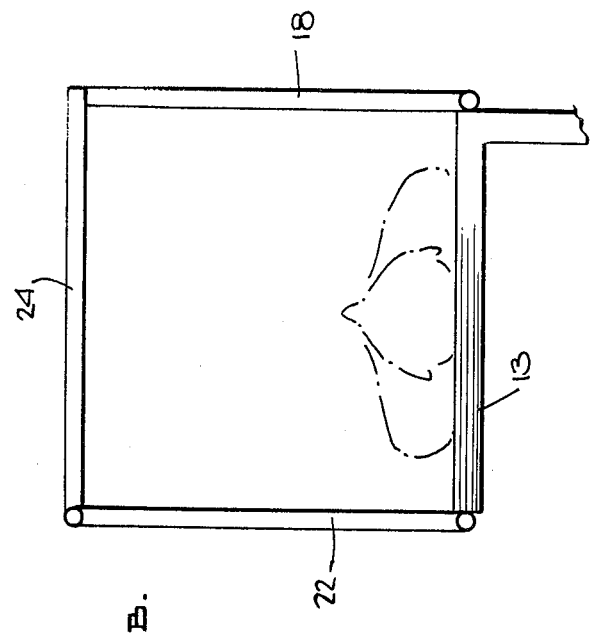
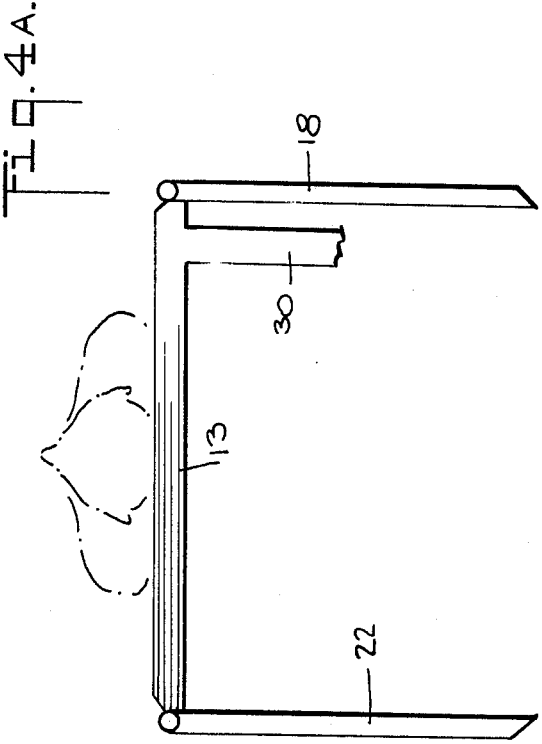
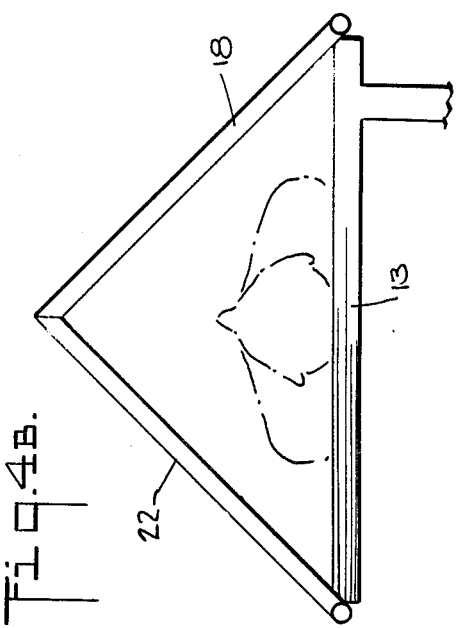

APPARATUS FOR IRRADIATING THE SKIN

In the past many apparatus have been described for the treatment or irradiation of the skin of a patient. In treating a patient having psoriasis, for example, the present treatment, termed photochemotherapy, consists of administering medication to the patient such as 8-methoxypsoralen (methoxysalen), a photoactive drug, followed by high intensity, longwave ultraviolet light radiation of the skin for periods of time. The apparatus used heretofore for the treatment generally comprises a cabinet or chamber in which the patient stands or reclines to receive the treatments which sometimes last from 15 minutes to about an hour. These cabinet devices suffer from several disadvantages. Firstly the patient must remain in a standing position for considerable periods of time depending on the amount of radiation required. This becomes extremely difficult for elderly patients or for patients who cannot stand. Secondly, by virtue of the heat developed by the radiation source and attendant electrical apparatus located in the chamber (i.e. lamps, transformers, ballasting equipment, etc.) uncomfortably high temperatures develop in the chamber. Heretofore the only method used to dissipate the heat is by natural convection whereby hot air is moved slowly out the top of the chamber. Generally 18 inches to 2 feet of free air space is required between the patient and chamber wall to maintain air circulation. Thirdly, these chambers are large, bulky and are usually too heavy to be conveniently moved elsewhere for storage. Since they occupy a large portion of a treatment room they can only be used either in a room set aside for their purpose only or in a room where space is not at a premium.

For example, in U.S. Pat. No. 3,877,437 to Maiton et al, an apparatus for phototherapy of the total skin of newborn children affected by haemolitic jaundice is described which enables the entire surface of the child's skin to be irradiated by fluorescent light simultaneously and in one treatment without having to change the position of the body. Generally, the apparatus comprises a movable trolley on which a chamber is mounted made entirely of transparent material. Above and below the trolley are a series of fluorescent tubes placed above reflecting sheets which concentrate the light rays given off by the tubes toward the bottom and top of the chamber.

In another U.S. patent to Gibbons, U.S. Pat. No. 2,960,986 a therapeutic heat and massage table is provided containing movable hinged reflecting hoods in the shape of half cylinders made of sheet metal material. The sheet material terminates above the top surface of the table to provide a clearance space for convection currents to circulate through and up over the body of the patient. The reflective hoods have a plurality of light bulbs attached to their inner surfaces. By selectively turning the bulbs on and off heat can be directed locally to any part of the body of the patient that requires treatment.

Although the apparatus described in these patents permits the patient to recline on a table for treatment they are nonetheless bulky and cumbersome and do not provide complete mobility and convenient storage of the apparatus, nor do they provide efficient means for removing the heat generated by their respective radiation sources.

The present invention provides an apparatus for treatment of the human skin, particularly for the treatment of psoriasis by photochemotherapy, which has the following advantages over apparatus described heretofore.

1. The patient rests on a table and can be uniformly irradiated by movable upper radiation units above the table;
2. The apparatus can be conveniently moved and stored in a treatment room because the radiation units can be moved to conform to the plane surfaces of a room (i.e. walls and ceilings). After the units are stored the table can be easily moved away from the units and used for other purposes such as for general treatments or examination of patients;
3. Means can be provided for the removal of heat from the area surrounding the patient; and
4. All electrical control equipment for the radiation source can be located at a remote site thereby saving space and removing an added source of unwanted heat to the patient.
5. The apparatus preferably employs a radiation transmissive table with a lower radiation unit located below the table at a fixed distance from the table for irradiating the bottom surface of the table. Both the lower radiation unit and the table can be vertically moved together to elevate the patient up toward the upper units or to lower the patient away from the upper units. In this manner, regardless of the size of the patient he can receive uniform radiation from above and below his body.

SUMMARY OF THE INVENTION

The apparatus of this invention comprises:
a. a base;
b. a substantially horizontal support member mounted on said base;
c. a first planar upper radiation unit positioned at one side of said support member in a plane extending upwardly from the upper portion of said support member, said first unit comprising a radiation source and a radiation transmissive material disposed between said radiation source and said support member;
d. an assembly of at least one other upper planar radiation unit comprising a radiation source and a radiation transmissive material, the one other upper radiation unit of the assembly being pivotably mounted with respect to the upper portion of the first radiation unit for movement about a substantially horizontal axis extending adjacent the plane in which the first radiation unit extends; means for selectively retaining the one other upper radiation unit of the assembly in a stored position extending upwardly with respect to the first upper radiation unit and in operating position extending in a facing relationship with the upper surface of the support member, each other upper radiation unit of the assembly being attached to the edge portion of the upper radiation unit adjacent thereto, which is nearest the first upper radiation unit.

The present apparatus can be used for many purposes as for example for heat and light energy exposure to the skin for therapeutic and healing purposes. The apparatus is particularly designed however, for the treatment of patients suffering from psoriasis. The treatment consists of orally administering a drug such as methoxysalen to the patient and then irradiating the area of the patient's skin where the psoriasis is evident with ultraviolet radiation by means of ultraviolet lamps to wavelengths of between about 320 and 400 nm for periods of 15 minutes to an hour. By virtue of the present apparatus, the patient is permitted to recline on a horizontal support member, i.e. a table and receive the ultraviolet radiation through one or more upper planar units comprising a plurality of ultraviolet lamps having a sheet of ultraviolet light transmissive material disposed between the lamps and the patient. The light transmissive material permits the beneficial radiation to pass to the patient and prevents the patient from accidentally touching the hot lamps or from breaking a lamp. A plurality of upper planar units connected edgewise in end to-end sequence and capable of pivotal movement with respect to one another are located above the table. The upper units are moved to form a perimeter around the top surface of the table by placement of the series of units from one side of the table to the opposite side. In the preferred embodiment of this invention, the horizontal support member is a table made of a sheet of light transmissive material and is attached to a vertically movable support member which comprises part of the base. Beneath the table at a fixed distance therefrom is a lower planar radiation unit comprising a plurality of ultraviolet lamps attached to the vertically movable support member. By moving the movable support member and hence the table and lower unit simultaneously and vertically upwards or downwards toward or away from the upper units, the patient can be positioned at equal distances from the upper most radiation unit and the lower unit irrespective of his size, i.e. obese or slender. While operating in concert with the upper units the entire surface or any portion of the patient's body can be exposed. By virtue of the movable arrangement of the upper units the apparatus may be attached to and stored against an existing wall with the upper units moved to conform to the plane surfaces of the wall or ceiling thus saving substantial cubical space volume. A series of fans or other means for circulating air around the patient may be installed in the wall of the treatment room adjacent the table to remove any heat developed by the ultraviolet lamps. A reflector or series of reflectors may be positioned behind the radiation source to concentrate the emitted radiation toward the patient. Heat exchanger elements can be located in the vicinity of the ultraviolet lamps to remove the heat generated therefrom.

The electrical control box and ballasting equipment for the ultraviolet lamps are located at a remote site from the apparatus thus preventing any heat generated from this equipment from reaching the patient. It has been found that by using a certain light transmissive material between the ultraviolet lamps and the patient, ultraviolet radiation which might cause skin burning of the patient, i.e. radiation of wavelengths below about 320 nm, can be filtered out while the beneficial radiation necessary for treatment is transmitted through the material.

The invention will be more completely described with reference to the drawings.

BRIEF DESCRIPTION OF THE DRAWINGS

FIG. 1 is a side view of the preferred embodiment of the present invention showing the upper movable radiation units in their stored position.

FIG. 2 is the same side view as in FIG. 1 but with all upper units positioned at the sides of the table in the operating position.

FIG. 4A illustrates an embodiment of the present invention having two upper radiation units each pivotably mounted on each side of the table.

FIG. 4B shows the units of FIG. 4A in their operating position above the table.

FIG. 5A illustrates an embodiment of the present invention having a first upper radiation unit positioned at one side of the table and two other upper radiation units, the first of which is pivotably mounted on the opposite side of the support table and the other being pivotably connected to the first other unit.

FIG. 5B shows the units of FIG. 5A in the operating position above the support member.

DETAILED DESCRIPTION OF THE PREFERRED EMBODIMENTS

Figure 3:
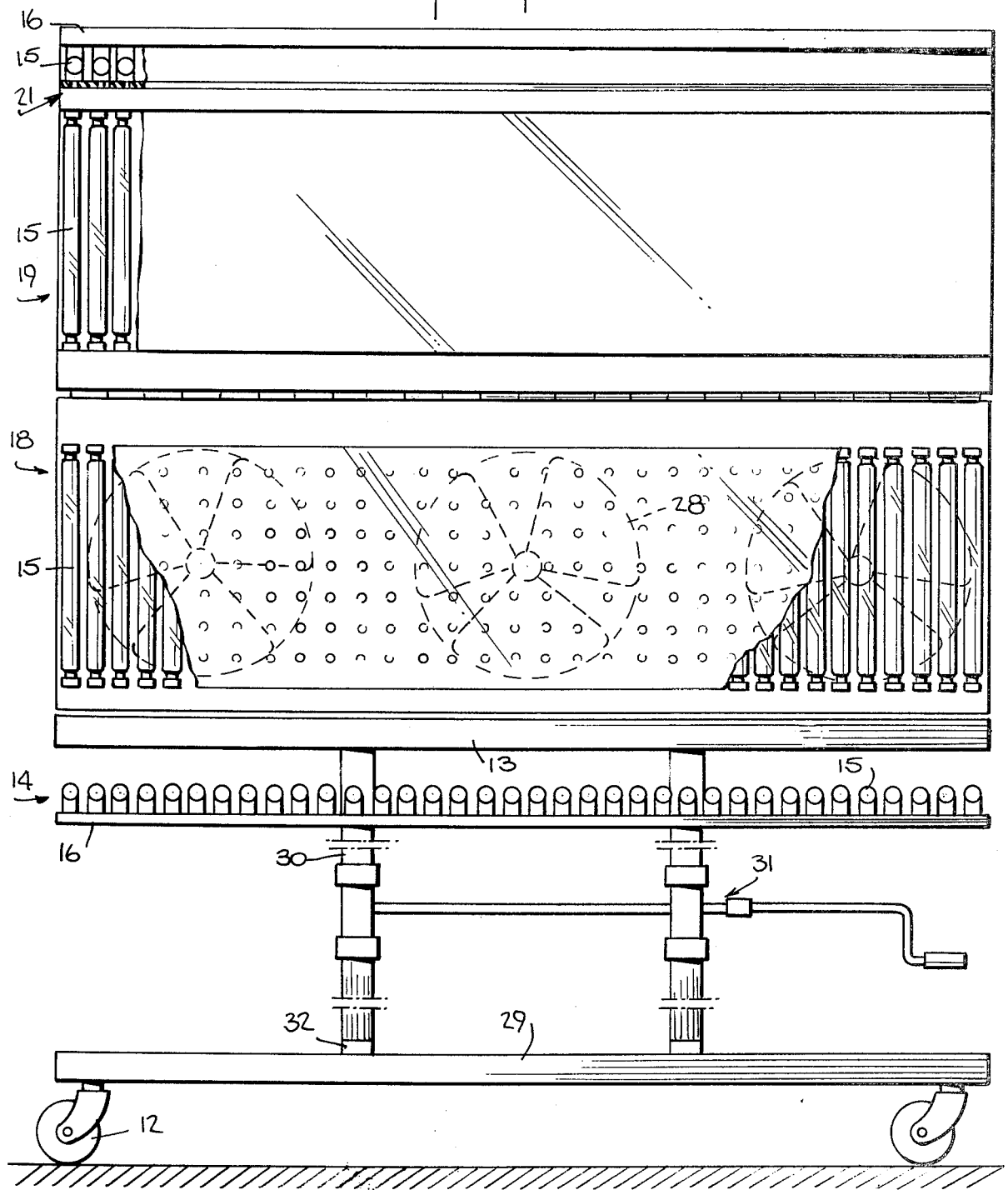
Fig. 3 is a front view of the apparatus.

Referring to FIG. 1, the preferred treatment apparatus 10 comprises a base 11 having a horizontal bottom member 29 and a fixed vertical member 32. Vertical member 30 is mounted to fixed vertical member 32 to be vertically movable with respect to the base by means 31 which can be a rack and pinion gear assembly, for example. Means 12 for moving the base 11 along a floor or other horizontal surface are mounted on bottom member 29. Wheels or casters have been found to be satisfactory. Horizontally mounted on vertical member 30 is a table 13 for supporting the patient to be treated in a reclining position. The table can be 2 to 3 feet wide, 5 to 10 feet long and about 1 to 3 inches thick for example. The table is comprised of a material which is capable of supporting the weight of the patient and will transmit the radiation to which the patient is to be exposed. In treating psoriasis the radiation should be in the ultraviolet range of wavelengths preferably between about 320 nm and 400 nm. An excellent material for this purpose is perforated Lucite or plexiglass. However any other radiating transmissive materials having similar characteristics may also be employed. The type of material used will depend on the radiation to be received by the patient. Lucite or plexiglass is preferably employed as the radiation transmissive material for ultraviolet radiation. A plexiglass material under the trade name UV-2 (Rohm & Haas) is particularly advantageous in treating a patient with psoriasis because although the beneficial ultravoilet radiation is transmitted by this material, the ultraviolet radiation that may cause burning of the patient's skin is absorbed or filtered out by this material.

It is not required that the radiation transmissive material be perforated. It may also be a solid sheet of transmissive material such as Lucite, plexiglass or UV-2 (Rohm & Haas) previously mentioned. By using a perforated material however there is a more direct exposure of radiation to the skin of the patient.

Below the table 13 is a lower planar radiation unit 14 mounted on a support member 16 which support member is attached to vertical member 30 at a fixed distance from the table. The lower unit comprises a radiation source which in FIGS. 1 and 2 is an array of ultraviolet lamps 15 capable of emitting the desired radiation. In treating psoriasis these lamps can be a number of 20, 40, or 60 watt lamps of various lengths i.e., 2', 3', 6', or longer.

Located above the table are a plurality of upper planar radiation units 18, 19 and 21 each comprising a radiation source 15 which is an array of ultraviolet lamps and a light transmissive sheet 17 having the same characteristics as the table 13 and can be perforated or non-perforated. Each unit is mounted on a support member 16 in the shape of a frame or solid sheet of metal which can be perforated or non-perforated. The lamps are of the same type used in connection with the lower planar unit 14 described above. The lamps of short length, i.e. 3 feet or less, can be arranged side by side as shown in FIG. 3 with their longitudinal axes extending along the width of their respective support members 16. The lamps of longer length, i.e. 6 feet or over, can be arranged side by side with their longitudinal axes extending along the length of their respective support members. First upper unit 18 is positioned at one side of table 13 in a plane extending above the table at 90° thereto. In the embodiment shown in FIG. 1 this unit is attached to unit bracket 25 which in turn is attached either permanently or temporarily as by a roller latch or catch to wall bracket 26 fixed to wall 33. However unit 18 may also be attached to the table or base if desired. Unit 18 may also be pivotably connected to the base or table to allow movement of from 0° to 90° with respect to the table. Upper unit 19 is pivotably connected edgewise to unit 18 by spring-loaded hinges 20 at their respective supporting members 16 and is capable of movement of 90° to 180° with respect to unit 18. The spring-loaded hinges 20 serve as means for retaining the unit in an upright position (viz. in the same plane as unit 18) when the apparatus is stored. Unit 21 is connected to unit 19 at the edges of their respective supporting members 16 and in FIGS. 1 and 2 unit 21 is connected to unit 19 at right angles thereto. This is depicted in the drawings to illustrate that unit 21 can conform to the plane of the ceiling 27 of a treatment room in its stored position. Unit 21 can however be also pivotably connected to unit 19 so as to be capable of movement from 90° to 180° with respect to unit 19. FIG. 2 shows the apparatus having unit 21 positioned at the side 23 of table 13 in the operating position. By virtue of this configuration the patient's entire body can be exposed to ultraviolet radiation. The units can be operated by a remote control box (not shown) through accompanying wiring to turn on any one, two, three or four of said units to administer treatments. The attachment of table 13 and lower unit 14 to movable member 30 permits height adjustment of the table and lower unit simultaneously toward or away from upper unit 19 when in the operating position (see FIG. 2). In this manner, depending on the size of the patient, the table can be adjusted to permit equal exposure from unit 19 and lower unit 14. The exposure from units 18 and 21 is essentially constant. If desired the table and lower unit may be fixedly mounted on the base through a single fixed vertical member.

On completion of the treatment the units are turned off and moved to be stored adjacent wall 33 and ceiling 27 as shown in FIG. 1.

Located in wall 33 is a fan 28 which blows air over the patient under treatment through the perforations in units 18 and 21 to remove heat generated by the lamps in units 14, 18, 19 and 21. If solid support members are used for units 18 and 21, they should also be perforated to permit air flow across the table. If a solid radiation transmissive sheet is used with these units then the fans may be mounted at the head or foot of the table for removing heat from the patient. Cooled air or an air conditioning unit may also be employed to remove heat.

The planar radiation units may also contain a reflecting sheet (not shown) behind the radiation source to concentrate the radiation given off by the lamps toward the patient. This reflecting sheet may be in the form of a single sheet or foil of a reflective metal such as stainless steel or aluminum behind the array of lamps or a number of individual sheets behind each lamp. A bank of heat exchanger tubes or other means for removing heat may be disposed between each lamp for removing heat generated by the lamps, to assist in preventing unwanted heat from reaching the patient. The tubes may be filled with gas or liquid such as water or any other heat conductive liquid and connected to a pump means for circulating the gas or liquid in the tubes.

It is preferred that the lower unit 14 be included in the apparatus. However, the patient can be treated by the upper units only to receive exposure over most of his body. If he requires treatment over the remainder of his body he can be turned over on the table to expose the remaining portion to the upper units.

It should be noted that according to FIGS. 1, 2 and 3 the preferred embodiment of the present invention contemplates a single fixed lower unit and three planar upper movable units 18, 19 and 21 connected edgewise in sequence and which when attached to both sides of table 13 form a threesided perimeter over the top surface of the table. However it is also within this invention to have 2 or more upper units which are pivotably connected and which cover the top surface of the table when in the operating position. For example, two upper units pivotably connected can be used to form a two-sided perimeter above the surface of the table and can be easily unfolded to conform to the contour of a wall. Similarly, a 4 or 5 upper unit arrangement can be designed to form a 4 or 5 sided perimeter above the surface of the table and can be unfolded to conform to the plane surfaces or wall and ceiling. The arrangement of three upper units as shown in the drawings however is most practical and is preferred.

It is also within the scope of this invention to have one upper radiation unit positioned at one side of the table and one or more units mounted at the opposite side of the table wherein the units can be engaged above the table to expose the patient.

FIG. 4A shows an embodiment of the invention wherein a first radiation unit 18 is pivotably mounted at one side of table 13 and another radiation unit 22 is pivotably mounted on the opposite side of the table. In FIG. 4B the two units are shown engaged above the table thus forming a two-sided perimeter above the top surface of the table.

FIG. 5A shows still another embodiment of the present invention, which in addition to having a first radiation unit 18 pivotably mounted at one side of table 13 and a second radiation unit 22 pivotably mounted on the opposite side of table 13 as in FIGS. 4A and 4B, a third radiation unit 24 pivotably mounted to unit 22. In FIG. 5B the three units are shown in position above the table with unit 24 engaging unit 18; thus forming a three-sided perimeter above the top surface of the table. It is also within the scope of this invention to have more than two units mounted as shown by 22 and 24 in FIGS. 5A and 5B with the free end of the last of said units capable of engagement with unit 18 to form a multisided perimeter over the top surface of the table.

What is claimed is:
1. An apparatus comprising:
 a. a base;
 b. a substantially horizontal support member mounted on said base;

c. a first planar upper radiation unit positioned at one side of said support member in a plane extending upwardly from the upper portion of said support member, said first unit comprising a radiation source and a radiation transmissive material disposed between said radiation source and said support member;

d. an assembly of at least one other upper planar radiation unit comprising a radiation source and a radiation transmissive material, the one other upper radiation unit of the assembly being pivotably mounted with respect to the upper portion of the first radiation unit for movement about a substantially horizontal axis extending adjacent the plane in which the first radiation unit extends; means for selectively retaining the one other upper radiation unit of the assembly in a stored position extending upwardly with respect to the first upper radiation unit and in operating position extending in a facing relationship with the upper surface of the support member, each other upper radiation unit of the assembly being attached to the edge portion of the upper radiation unit adjacent thereto which is nearest the first upper radiation unit.

2. The apparatus of claim 1 wherein said base is movable.

3. The apparatus of claim 1 wherein said support member is comprised of a solid radiation transmissive material.

4. The apparatus of claim 3 which further comprises a lower planar radiation unit positioned beneath said support member; said unit comprising a radiation source.

5. The apparatus of claim 4 wherein said support member and said lower radiation unit are mounted on a support member, said member attached to said base in a vertically movable manner.

6. The apparatus of claim 1 wherein said radiation transmissive material is selected from the Group consisting of Lucite and plexiglass.

7. The apparatus of claim 1 wherein said radiation transmissive material contains perfortions.

8. The apparatus of claim 1 wherein said radiation source is a plurality of ultraviolet lamps.

9. The apparatus of claim 1 wherein each other upper radiation unit is pivotably attached to the edge portion of the upper radiation unit adjacent thereto.

10. An apparatus comprising:
a. a base;
b. a substantially horizontal support member mounted on said base;
c. a first planar upper radiation unit positioned at one side of said support member in a plane extending upwardly from the upper portion of said support member, said first unit comprising a radiation source and a radiation transmissive material disposed between said radiation source and said support member;
d. an assembly of at least one other upper planar radiation unit positioned at the side of said support member opposite to the side where said first unit is positioned, means for selectively retaining the one other upper radiation unit of the assembly in a stored position extending above or below the surface of said support member, and in operating position extending in a facing relationship with the upper surface of the support member, each other upper radiation unit of the assembly being pivotably attached to the edge portion of the other upper radiation unit adjacent thereto which is nearest the first other upper radiation unit.

11. The apparatus of claim 10 wherein said base is movable.

12. The apparatus of claim 10 wherein said support member is comprised of a solid radiation transmissive material.

13. The apparatus of claim 12 which further comprises a lower planar radiation unit positioned beneath said support member; said unit comprising a radiation source.

14. The apparatus of claim 13 wherein said support member and said lower radiation unit are mounted on a support member, said member attached to said base in a vertically movable manner.

15. The apparatus of claim 10 wherein said radiation transmissive material is selected from the Group consisting of Lucite and plexiglass.

16. The apparatus of claim 10 wherein said radiation transmissive material contains perforations.

17. The apparatus of claim 10 wherein said radiation source is a plurality of ultraviolet lamps.

18. An apparatus for treating the skin of a patient having psoriasis comprising:
a. a movable base;
b. a table mounted on said base for receiving the patient for treatment; said table being comprised of a solid radiation transmissive material;
c. a lower planar radiation unit positioned beneath said table, said unit comprising a plurality of ultraviolet lamps;
d. a first planar upper radiation unit fixedly mounted at one end at the side of said table and extending above said table at a right angle to the surface of said table; said first upper unit comprising a plurality of ultraviolet lamps and a solid ultraviolet radiation transmissive sheet between said lamps and said table;
e. a second planar upper radiation unit pivotably connected to the upper portion of said first upper unit for movement about a horizontal axis adjacent the plane in which the first radiation unit extends; said unit comprising a plurality of ultraviolet lamps and a solid radiation transmissive sheet between said lamps and said table;
f. a third upper planar radiation unit fixedly connected to the upper portion of said second upper unit at a right angle thereto facing the upper surface of said table; said unit comprising a plurality of ultraviolet lamps and a solid radiation transmissive sheet between said lamps and said table.

19. The apparatus of claim 18 wherein said solid radiation transmissive sheet is selected from the group consisting of Lucite and plexiglass.

20. The apparatus of claim 19 wherein said sheet is perforated.

21. The apparatus of claim 18 which further comprises means for removing heat generated by said lamps from said apparatus.

22. The apparatus of claim 21 wherein said heat removing means is a fan.

23. The apparatus of claim 21 wherein said heat removing means is a heat exchanger element located near the surface of said lamps.

24. The apparatus of claim 18 which further comprises a sheet of a reflective metal mounted behind said lamps to concentrate radiation to said patient.

25. The apparatus of claim 18 wherein said table and said lower radiation unit are mounted on a support member, said member attached to said base in a vertically movable manner.

26. An apparatus for treating the skin of a patient having psoriasis comprising:

a. a movable base having a support member attached to said base in a vertically movable manner;

b. a table mounted on said member for receiving the patient for treatment; said table being comprised of a solid radiation transmissive material;

c. a lower planar radiation unit mounted on said member at a fixed distance beneath said table, said unit comprising a plurality of ultraviolet lamps;

d. a first planar upper radiation unit positioned at one end at the side of said table and extending above said table at a right angle to the surface of said table; said first upper unit comprising a plurality of ultraviolet lamps and a solid ultraviolet radiation transmissive sheet between said lamps and said table;

e. a second planar upper radiation unit pivotably connected to the upper portion of said first upper unit for movement about a horizontal axis adjacent the plane in which the first radiation unit extends; said unit comprising a plurality of ultraviolet lamps and a solid radiation transmissive sheet between said lamps and said table;

f. a third upper planar radiation unit fixedly connected to the upper portion of said second upper unit at a right angle thereto facing the upper surface of said table; said unit comprising a plurality of ultraviolet lamps and a solid radiation transmissive sheet between said lamps and said table.

* * * * *